(12) United States Patent
Kim et al.

(10) Patent No.: US 9,518,149 B2
(45) Date of Patent: Dec. 13, 2016

(54) HIGHLY PURIFIED POLYLACTIC ACID OR A DERIVATIVE THEREOF, A SALT OF THE SAME, AND PURIFICATION METHOD THEREOF

(75) Inventors: Bong Oh Kim, Daejeon (KR); Min Hyo Seo, Daejeon (KR)

(73) Assignee: SAMYANG BIOPHARMACEUTICALS CORPORATION (KR)

( * ) Notice: Subject to any disclaimer, the term of this patent is extended or adjusted under 35 U.S.C. 154(b) by 693 days.

(21) Appl. No.: 13/126,395

(22) PCT Filed: Jun. 23, 2009

(86) PCT No.: PCT/KR2009/003366
§ 371 (c)(1),
(2), (4) Date: Apr. 27, 2011

(87) PCT Pub. No.: WO2010/053242
PCT Pub. Date: May 14, 2010

(65) Prior Publication Data
US 2011/0207834 A1  Aug. 25, 2011

(30) Foreign Application Priority Data
Nov. 7, 2008  (KR) .................. 10-2008-0110348

(51) Int. Cl.
| C08G 63/90 | (2006.01) |
| C08C 1/14 | (2006.01) |
| A61K 31/21 | (2006.01) |
| A61K 31/12 | (2006.01) |
| A61K 47/00 | (2006.01) |
| C08G 63/08 | (2006.01) |

(52) U.S. Cl.
CPC .............. C08G 63/90 (2013.01); C08G 63/08 (2013.01)

(58) Field of Classification Search
USPC .............. 514/772.1, 506, 675, 785; 528/488
See application file for complete search history.

(56) References Cited

U.S. PATENT DOCUMENTS

| 4,797,468 A | 1/1989 | De Vries |
| 4,810,775 A * | 3/1989 | Bendix et al. ............... 528/480 |
| 5,585,460 A * | 12/1996 | Yamada et al. ............. 528/491 |
| 2005/0201972 A1* | 9/2005 | Seo et al. ................. 424/78.27 |
| 2007/0003625 A1 | 1/2007 | Seo et al. |

FOREIGN PATENT DOCUMENTS

| CA | 2 686 045 A1 | 11/2008 |
| CN | 1234387 A | 11/1999 |
| CN | 1780868 A | 5/2006 |
| CN | 101240061 A | 8/2008 |
| JP | 4-218528 A | 8/1992 |
| WO | WO 2005/054333 A1 | 6/2005 |
| WO | WO 2005/105886 A1 | 11/2005 |
| WO | WO 2006/001034 A2 | 1/2006 |

OTHER PUBLICATIONS

Avgoustakis, Current Drug Delivery, 2004, vol. I, No, 4, 321-333.*
Matkovich, Analytical Chemistry, 1973, 1915-1920.*
International Search Report for corresponding PCT application No. PCT/KR2009/003366 mailed Feb. 5, 2010.
Form PCT/ISA/237 for corresponding PCT application No. PCT/KR2009/003366.
Office Action mailed Jul. 3, 2012 for Canadian Patent Application No. 2,742,361.
Office Action for Chinese Patent Application No. 200980144492.9 (mailed Aug. 3, 2012).
Extended European Search Report for European Patent Application No. 09824925.3 mailed Sep. 12, 2013.
Office Action for Chinese Patent Application No. 20098014492.9 (mailed Dec. 4, 2013).

\* cited by examiner

*Primary Examiner* — Shobha Kantamneni
(74) *Attorney, Agent, or Firm* — Merchant & Gould P.C.

(57) ABSTRACT

Disclosed are a highly purified polylactic acid or a derivative thereof, or a salt thereof, and a method for purifying the same. The polylactic acid or a derivative thereof, or a salt thereof may be applied to various medical and drug carrier systems, or the like.

3 Claims, 2 Drawing Sheets $$HO-C(=O)-[-CH(CH_3)-O-C(=O)-]_n-CH(CH_3)-OH$$

$$HO-C(=O)-[-CH(CH_3)-O-C(=O)-]_n-CH(CH_3)-OH$$

HIGHLY PURIFIED POLYLACTIC ACID OR A DERIVATIVE THEREOF, A SALT OF THE SAME, AND PURIFICATION METHOD THEREOF

This application is a National Stage Application of PCT/KR2009/003366, filed 23 Jun. 2009, which claims benefit of Serial No. 10-2008-0110348, filed 7 Nov. 2008 in the Republic of Korea and which applications are incorporated herein by reference. To the extent appropriate, a claim of priority is made to each of the above disclosed applications.

TECHNICAL FIELD

This disclosure relates to a polylactic acid or a derivative thereof, or a salt thereof with high purity, and a method for purifying the same.

BACKGROUND ART

Polylactic acid is one of biodegradable polymers, and has been applied to drug carriers in various forms because it has excellent biocompatibility and it is hydrolyzed into lactic acid non-harmful to the human body. Polylactic acid derivatives including a polylactic acid have various properties depending on molecular weight. For example, a polylactic acid derivative having a molecular weight of 2000 daltons or higher is not soluble in water, and thus has been developed into microspheres, nanoparticles, polymeric gels and implant agents.

In addition, polylactic acid derivatives used as drug carriers may be modified in terms of molecular weight and copolymer constitution to control drug release rate. In controlling drug release rate, purity of a polylactic acid derivative plays an important role. During the polymerization of a polymer from monomers, unreacted monomers may remain in the polymer to decrease the purity of the polylactic acid derivative. If the content of unreacted monomers is high, the polylactic acid derivative has a broad molecular weight distribution. As a result, administration of a low-molecular weight polymer molecule into the human body may cause excessive drug release at the initial time. Moreover, while the remaining monomers are decomposed, pH decreases and the polymer decomposition rate increases. This makes it difficult to accomplish prolonged drug release.

According to the related art, a polylactic acid is purified by a solvent/non-solvent method. The method is advantageous in that a solidified polymer may be obtained, when the polymer has a high molecular weight or when preparing an L,L-polylactic acid derivative. However, when the polymer has a low molecular weight or when preparing non-crystalline D,L-polylactic acid derivatives, gel-like precipitate is generated upon settling in a non-solvent, making it difficult to purify the polymer.

Particularly, in the case of D,L-polylactic acid with a low molecular weight, precipitation of its acetone solution in distilled water causes generation of gel-like precipitate. Such gel-like precipitate hardly allows moisture removal even when subjected to vacuum drying. Thus, removing moisture needs a long time. In addition, under the high-temperature vacuum condition, condensation polymerization may occur, making it difficult to control the molecular weight. Further, under the same condition, lactide monomers may be produced.

Additionally, when the polymer has a high molecular weight or when preparing crystalline L,L-polylactic acid, solidified polylactic acid may be obtained through the above-mentioned solvent/non-solvent method. However, during the purification based on the solvent/non-solvent method, the monomers and an organometal catalyst may co-precipitate in the non-solvent and be not removed effectively therefrom.

Meanwhile, a method for purifying D,L-polylactic acid with a low molecular weight by liquid-liquid phase separation is also known. After the polymerization, the polymer is dissolved in methanol or ethanol under heating. Then, the polymer solution is refrigerated at a temperature of −78° C. so that phase separation occurs. Polylactic acid with a low molecular weight is dissolved in the upper organic solvent layer, while polylactic acid with a high molecular weight is solidified in the lower layer. The lower layer is separated and the solvent is distilled off to remove the monomers and oligomers. In this manner, highly purified D,L-polylactic acid having a narrow molecular weight distribution is provided. However, the lactide monomers produced during the polymerization is dissolved in an alcohol solvent at high temperature but recrystallized therein at low temperature. Therefore, the monomers are not removed effectively from D,L-polylactic acid even after carrying out the above method.

DISCLOSURE

Technical Problem

Provided is a method for effectively purifying a polylactic acid or a derivative thereof, or a salt thereof.

Also provided is a polylactic acid or a derivative thereof, or a salt thereof with high purity.

Further provided is a pharmaceutical composition including a polylactic acid or a derivative thereof, or a salt thereof with high purity.

Technical Solution

Disclosed herein is a polylactic acid or a derivative thereof, or a salt thereof with high purity. Disclosed herein too is a method for purifying the same. More particularly, the method includes: dissolving a polylactic acid or a derivative thereof, or a salt thereof into a water-miscible organic solvent; adding water or an aqueous alkali metal salt solution to the solution of polymer dissolved in the organic solvent, followed by mixing; subjecting the mixture to phase separation to remove water and to recover the organic solvent layer; and removing the organic solvent from the organic solvent layer to recover the polymer. In addition, the polylactic acid or a derivative thereof, or a salt thereof disclosed herein has a lactone monomer content of 1.0 wt % or less and a content of metal in an organometal catalyst of 50 ppm or less.

Advantageous Effects

According to the method disclosed herein, it is possible to obtain a highly purified polylactic acid or a derivative thereof, or a salt thereof, from which unreacted monomers, oligomers, and metals are removed effectively.

DESCRIPTION OF DRAWINGS

The above and other aspects, features and advantages of the disclosed exemplary embodiments will be more apparent from the following detailed description taken in conjunction with the accompanying drawings in which.

MODE FOR INVENTION

Figure 1:
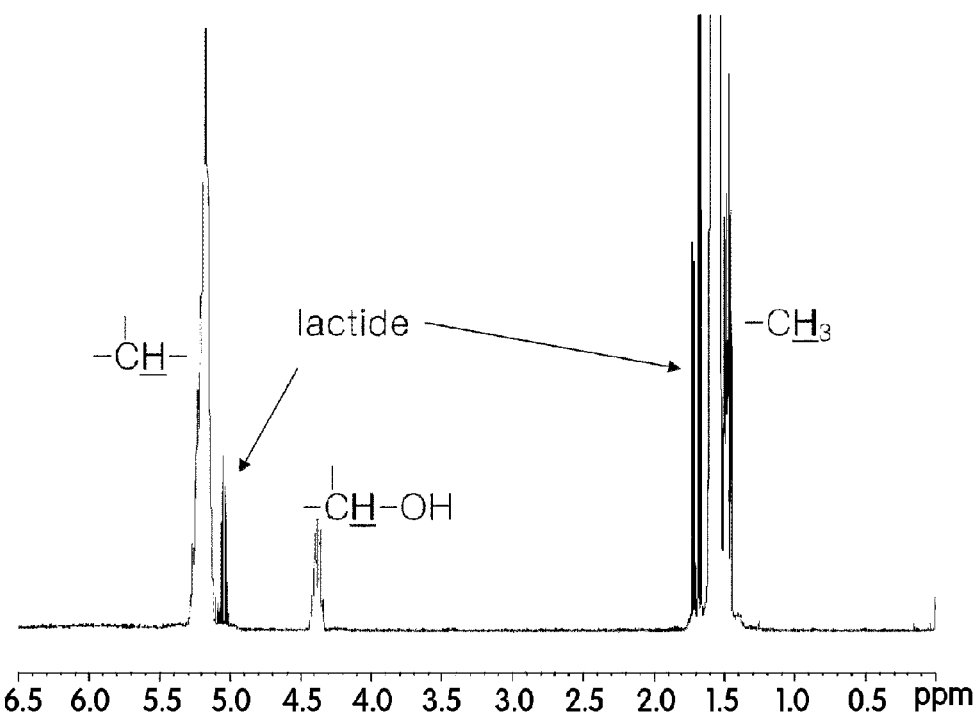
FIG. 1 is the ¹H-NMR spectrum of D,L-polylactic acid obtained from Preparation Example 1.

Exemplary embodiments now will be described more fully hereinafter with reference to the accompanying drawings, in which exemplary embodiments are shown. This disclosure may, however, be embodied in many different forms and should not be construed as limited to the exemplary embodiments set forth therein. Rather, these exemplary embodiments are provided so that this disclosure will be thorough and complete, and will fully convey the scope of this disclosure to those skilled in the art. In the description, details of well-known features and techniques may be omitted to avoid unnecessarily obscuring the presented embodiments.

The terminology used herein is for the purpose of describing particular embodiments only and is not intended to be limiting of this disclosure. As used herein, the singular forms "a", "an" and "the" are intended to include the plural forms as well, unless the context clearly indicates otherwise. Furthermore, the use of the terms a, an, etc. does not denote a limitation of quantity, but rather denotes the presence of at least one of the referenced item. It will be further understood that the terms "comprises" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

In one aspect, there is provided a method for purifying a polylactic acid or a derivative thereof, or a salt thereof. Particularly, the method enables preparation of a polylactic acid or a derivative thereof, or a salt thereof, having a lactone content of 1.0 wt % or less and a content of metal in an organometal catalyst of 50 ppm or less, particularly 20 ppm or less.

The lactone monomers, and hydrolyzates and low-molecular weight oligomers thereof are decomposed easily in vivo and in an aqueous solution, resulting in a drop in pH. Thus, decomposition of the polymer is accelerated and the stability of a drug contained in the polymer is affected thereby, resulting in generation of impurities. In addition, the organometal catalyst contained in the polymer as a foreign material accelerates hydrolysis of the polymer, resulting in a decrease in the molecular weight of the polymer, and thus a drop in pH. When the hydrolysis of the polymer is accelerated by the organometal catalyst, the polymer used in a formulated composition as a drug carrier is hindered in continuous drug release. Therefore, the polymer may cause undesirably earlier drug release, making it difficult to control the drug release rate. Therefore, in drug delivery systems using a polylactic acid or a derivative thereof, or a salt thereof, it is required to control the amount of monomers and low-molecular weight oligomers and the organometal catalyst content in order to control the drug release rate and to prevent generation of impurities.

When the lactone monomer content is greater than 1.0 wt %, decomposition of the polymer is accelerated to adversely affect the stability of the drug contained in the polymer, leading to generation of impurities. In addition, when the content of the metal in an organometal catalyst is in excess of 50 ppm, hydrolysis of the polymer is accelerated and pH is decreased, resulting in failure of continuous drug release.

Therefore, disclosed herein is a method for purifying a polylactic acid or a derivative thereof, or a salt thereof by effectively removing unreacted monomers, oligomers or an organometal catalyst remaining in crude polymer during the preparation thereof, so that a highly purified polymer may be provided.

The term 'polyactic acid' means a polymer polymerized from lactide or lactic acid, wherein the polylactic acid may be end-capped with a hydroxyl or carboxyl group.

In another embodiment, the 'polyactic acid derivative' may be at least one compound(s) selected from the group consisting of polylactide, polyglycolide, polymandelic acid, polycaprolactone, polydioxane-2-one, polyaminoacids, polyorthoesters, polyanhydrides and copolymers thereof. Particularly, the polylactic acid derivative may include polylactide, polyglycolide, polycaprolactone or polydioxane-2-one.

Particular examples of a polylactic acid or a derivative thereof may include at least one compound(s) selected from the group consisting of polylactic acid, copolymers of lactic acid with mandelic acid, copolymers of lactic acid with glycolic acid, copolymers of lactic acid with caprolactone, and copolymers of lactic acid with 1,4-dioxane-2-one.

Unless the context clearly indicates otherwise, it is understood that the term 'polyactic acid' or 'polyactic acid derivative' when used in this specification, means polylactic acid and polylactic acid derivative collectively because there is no differences in the purification method between polylactic acid and polylactic acid derivative.

In still another embodiment, the salt of polylactic acid or polylactic acid derivative may include an alkali metal salt of polylactic acid or polylactic acid derivative. Particularly, the alkali metal salt may include a metal ion salt of monovalent metal ion selected from sodium, potassium and lithium.

In one example embodiment, the polylactic acid or a derivative thereof, or a salt thereof may have a number average molecular weight of 500-20,000 daltons, specifically 500-10,000 daltons, and more specifically 500-5,000 daltons.

Particular embodiments of methods for preparing a polylactic acid or a derivative thereof as a starting material will be explained hereinafter.

In one embodiment, a ring opening polymerization process is carried out using lactone, such as L-lactide or D,L-lactide, as monomer. As an initiator, a hydroxyl group-containing compound may be used. For example, an alcohol with a high boiling point may be used. Particular examples of such alcohols include lauryl alcohol, 1,6-hexanediol, etc.

In addition to the initiator, an organometal catalyst is used so that the monomers are polymerized by the hydroxyl groups of the initiator. Particularly, when preparing a polylactic acid derivative for medical use, stannous octoate, approved by FDA as a medically acceptable catalyst, is generally used as a catalyst. The ring opening polymerization process is used for preparing a high-molecular weight polylactic acid derivative. The polylactic acid derivative prepared from the ring opening polymerization process still contains unreacted monomers and the organometal compound added as a catalyst.

In another embodiment, condensation polymerization is carried out using free acid, such as lactic acid. The condensation polymerization process is useful for preparing polylactic acid with a low molecular weight. This is because the condensation polymerization process does not allow easy and effective removal of water produced as a byproduct. To remove water as a byproduct, melt condensation polymerization may be carried out under a high-temperature vacuum condition. Otherwise, solution polymerization may be carried out using a water immiscible organic solvent in a reactor equipped with a Dean-Stark trap. The condensation polymerization process using lactic acid is useful for preparing a polylactic acid or derivatives thereof having a low molecular weight of 5,000 daltons or less. In this case, the polymerization may be performed without adding any catalyst. Polymerization of lactic acid via polycondensation provides polylactic acid still containing unreacted lactic acid and lactide generated under the high-temperature vacuum condition.

The polylactic acid or a derivative thereof, or a salt thereof obtained by the above-mentioned ring opening polymerization or condensation polymerization process includes a certain amount of unreacted monomers, i.e., lactide and lactic acid, oligomers thereof and organometal catalyst. The monomers, oligomers and organometal catalyst contained in the resultant crude polymer may be easily decomposed in vivo and in an aqueous solution, resulting in a drop in pH (acidification). As a result, decomposition of the polymer may be accelerated. When the hydrolysis of the polymer is accelerated by such impurities, the polymer used in a formulated composition as a drug carrier is hindered in sustained drug release and causes undesirably earlier drug release, making it difficult to control the drug release rate.

Therefore, disclosed herein is a method for purifying a polylactic acid or a derivative thereof, or a salt thereof by effectively removing byproducts or impurities generated during the preparation thereof, so that a polylactic acid or a derivative thereof, or a salt thereof with high purity may be provided.

According to one embodiment of the method for purifying a polylactic acid or a derivative thereof, or a salt thereof disclosed herein, the method includes: dissolving a polylactic acid or a derivative thereof, or a salt thereof into a water-miscible organic solvent; adding water or an aqueous alkali metal salt solution to the solution of polymer dissolved in the organic solvent, followed by mixing; subjecting the mixture to phase separation to remove water and to recover the organic solvent layer; and removing the organic solvent from the organic solvent layer to recover the polymer.

The method disclosed herein may be applied to polylactic acid or a derivative thereof with a low molecular weight.

First, a polylactic acid or a derivative thereof, or a salt thereof is dissolved into a water-miscible organic solvent to provide a polymer solution. For example, the organic solvent may be one capable of solubilizing the polymer and may include a water-compatible organic solvent having a boiling point of 100° C. or lower. Particularly, the organic solvent may include acetone or acetonitrile.

Next, water or an aqueous alkali metal salt solution is added to the solution of polymer dissolved in the organic solvent. Particularly, water or an aqueous alkali metal salt solution is gradually added to the organic solvent in which a polylactic acid or a derivative thereof, or a salt thereof is dissolved to hydrolyze unreacted monomers and oligomers. For example, the aqueous alkali metal salt solution has a concentration of 0.05-0.1 g/mL. Although the amount of water or the aqueous alkali metal salt solution is determined by the unreacted monomer content and the amount of the organic solvent, water or the aqueous alkali metal salt solution may be added in an amount corresponding to 0.5-2 times of the volume of the organic solvent.

In addition to the above role of the aqueous alkali metal salt, when the aqueous alkali metal salt solution is added to the polymer solution, it is possible to obtain a polylactic acid salt, a polylactic acid whose carboxy groups are replaced with alkali metal carboxylate, from a polylactic acid having carboxylic acid group at an end at this step. For example, the alkali metal salt may be at least one metal salt(s) selected from the group consisting of sodium bicarbonate, sodium carbonate, potassium bicarbonate, potassium carbonate and lithium carbonate. The particular type of alkali metal salt determines the metal ionically bonded with the carboxyl group of the polylactic acid salt end-capped with a carboxyl group such as the compound of Chemical Formula 2 or 3. Particularly, the aqueous alkali metal salt solution may be an aqueous sodium bicarbonate or potassium bicarbonate solution. Meanwhile, when adding water to the polymer solution, polylactic acid end-capped with a carboxylic acid having proton is provided.

In one example embodiment, the mixing operation may be carried out by agitating the mixture at 40-100° C. for 10 minutes to 24 hours. Particularly, the mixing operation includes agitating the mixture at 60-80° C. for 2-6 hours. During the agitation under heating, low-molecular weight polylactic acids and monomers are hydrolyzed. When using an alkali metal salt, neutralization occurs between the alkali metal salt, and low-molecular weight polylactic acids and monomers to provide salt compounds. Since the salt compound has high solubility to an aqueous solution, it facilitates purification via phase separation. The heating temperature and agitation time in the mixing operation are designed to facilitate hydrolysis and salt formation. For example, if the heating temperature is too high, the polylactic acid may undergo hydrolysis after the preparation thereof, leading to a decrease in molecular weight.

Then, the mixture is left to be phase-separated. In another example embodiment, the phase separation may be improved by adding a salt to the mixture so that the mixture is separated into an organic solvent layer and an aqueous layer. For example, the salt may include sodium chloride or potassium chloride. The separation using a salt may be carried out, for example, by adding sodium chloride to the mixture after the hydrolysis so that the solution is separated into the water-miscible organic solvent layer and an aqueous layer. After the phase separation, only the purified polymer is dissolved in the organic solvent layer, while the salt compound, alkali metal salt, unreacted monomers and oligomers and organometal catalyst are dissolved in the aqueous layer. When the polylactic acid or a derivative thereof is end-capped with a carboxylic acid having proton, phase separation may occur without adding any salt, because the polymer is not dissolved in water.

After the phase separation, the organic solvent is removed from the organic solvent layer to recover the polymer. For example, the organic solvent is removed from the organic solvent layer via fractional distillation. For example, the fractional distillation may be carried out at a temperature of 60-80° C.

In still another embodiment, the method may further include, after removing the solvent to recover the polymer: dissolving the recovered polymer into an anhydrous organic solvent, followed by filtering, to obtain a polymer-containing organic solvent; and removing the anhydrous organic solvent from the polymer-containing organic solvent.

For example, the anhydrous organic solvent may be anhydrous acetone or anhydrous acetonitrile.

In the filtering operation to obtain the polymer-containing organic solvent, a polylactic acid or a derivative thereof, or a salt thereof, from which the originally used water-miscible organic solvent is removed, is dissolved back into the anhydrous organic solvent. In this manner, the polymer is dissolved in the anhydrous organic solvent, while a small amount of salt compound such as sodium chloride or sodium bicarbonate, and alkali metal salt are precipitated. The precipitated compounds are removed by centrifugal separation or filtering.

Then, when removing the anhydrous organic solvent from the polymer-containing organic solvent, the polymer, from which the salt such as sodium chloride is removed, is further subjected to distillation to remove the organic solvent. For example, the distillation may be carried out at a temperature of 60-80° C. After removing the organic solvent, the purified polymer may be provided.

In a particular embodiment, the polylactic acid or a derivative thereof, or a salt thereof disclosed herein may include a monomer represented by Chemical Formula 1:

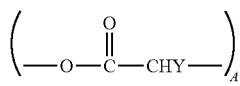

[Chemical Formula 1]

wherein
Y represents H, methyl or phenyl; and
A represents an integer from 5 to 300.

In a more particular embodiment, the polylactic acid or a derivative thereof, or a salt thereof may be represented by Chemical Formula 2 or 3:

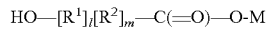

[Chemical Formula 2]

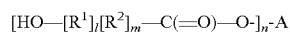

[Chemical Formula 3]

wherein
$R^1$ represents —C(=O)—O—CHZ—;
$R^2$ represents —C(=O)—O—CHY—, —C(=O)—O—CH$_2$CH$_2$CH$_2$CH$_2$CH$_2$— or —C(=O)—O—CH$_2$CH$_2$OCH$_2$—;
Z and Y independently represent H, methyl or phenyl;
l and m represent an integer from 0 to 150, with the proviso that both cannot represent 0 at the same time;
M represents H, Na, K or Li;
A represents a diol or a polyol compound containing 3-12 hydroxyl groups; and
n represents an integer from 2 to 12 and is the same as the number of hydroxyl groups contained in A.

More particularly, the compound containing 2-12 hydroxyl groups may include a single compound, such as an alcohol, diol compound, glycerol, pentaerythritol or xylitol, or a polymeric compound, such as polyethylene glycol or monomethoxypolyethylene glycol.

In another aspect, there is provided a polylactic acid or a derivative thereof, or a salt thereof with high purity. In one embodiment, the polylactic acid or a derivative thereof, or a salt thereof has a lactone monomer content of 1.0 wt % or less and a content of metal in an organometal catalyst of 50 ppm or less, particularly 20 ppm or less.

In still another aspect, there is provided a pharmaceutical composition including a polylactic acid or a derivative thereof, or a salt thereof. The polymer has excellent biocompatibility and is not harmful to the human body, and thus may be used as a drug carrier in various forms. In addition, the polymer may be modified in terms of molecular weight or copolymer constitution to control drug release rate. To accomplish this, highly purified polymer is required.

The pharmaceutical composition may further include pharmaceutical adjuvants, such as a preservative, stabilizer, hydrating agent or emulsification accelerator, osmotic pressure-adjusting salt and/or buffer, and other therapeutically effective materials. In addition, the pharmaceutical composition may be formulated into various oral or parenteral administration forms depending on administration route according to a method generally known to those skilled in the art.

The examples and experiments will now be described. The following examples and experiments are for illustrative purposes only and not intended to limit the scope of this disclosure.

Preparation Example 1

Synthesis of D,L-polylactic acid (PLA-COOH) via polycondensation

First, 1,000 g of D,L-lactic acid was introduced into a 2,000 mL three-necked round bottom flask and an agitator was mounted to the flask. Next, the flask was treated for 1 hour while being heated in an oil bath at 80° C. and depressurized to 25 mmHg with a depressurization aspirator to remove an excessive amount of water.

Then, the temperature was increased to 160° C. and the reaction was continued for 6 hours under a reduced pressure of 5-10 mmHg, before the reaction was terminated. After the reaction, 646 g of crude polylactic acid was obtained. The polylactic acid was analyzed by NMR and the results are shown in FIG. 1.

Preparation Example 2

Synthesis of D,L-polylactic acid (PLA-COOH) via ring opening polymerization

First, 500 g of D,L-lactide was introduced into a one-neck flask and vacuum dried at 50° C. for 4 hours. After the flask was cooled to room temperature, tin octoate catalyst (250 mg, 0.05 wt %) dissolved in toluene (0.5 mL) and 62.5 g of 1-dodecanol were introduced to the flask, and vacuum dried for 2 hours. The flask was purged with nitrogen gas, and polymerization was performed at 130° C. for 6 hours. After the polymerization, 380 g of crude polylactic acid was obtained.

Comparative Example 1

Purification of D,L-polylactic Acid (PLA-COOH)

Figure 2:
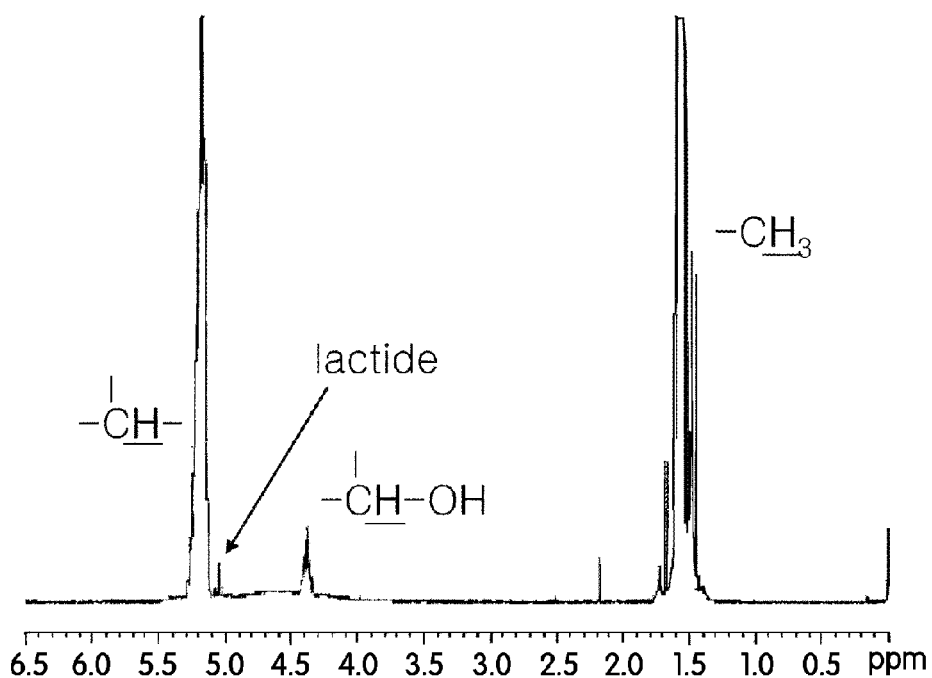
FIG. 2 is the ¹H-NMR spectrum of D,L-polylactic acid purified according to Comparative Example 1.

First, 100 mL of acetone was added to 100 g of the polylactic acid obtained from Preparation Example 1 to dissolve the polymer. Next, the polymer solution was gradually added to 1,000 mL of distilled water to precipitate the polymer. The precipitated polymer was filtered and washed with 500 mL of distilled water twice. To remove an excessive amount of water, the polymer was vacuum dried at 90° C. for 2 hours. After drying, 87 g of purified polylactic acid was obtained. The purified polylactic acid was analyzed by NMR and the results are shown in FIG. 2.

Comparative Example 2

Purification of D,L-polylactic Acid (PLA-COOH)

First, 100 mL of methylene chloride was added to 100 g of the polylactic acid obtained from Preparation Example 2 to dissolve the polymer. Next, the polymer solution was gradually added to 1,000 mL of diethyl ether to precipitate the polymer. Then, the precipitated polymer was filtered. The polymer was vacuum dried at room temperature. After drying, 66 g of purified polylactic acid was obtained.

Example 1

Purification of D,L-polylactic Acid (PLA-COOOH)

Figure 3:
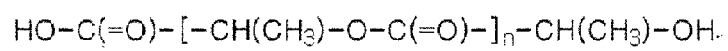
FIG. 3 is the ¹H-NMR spectrum of D,L-polylactic acid purified according to Example 1.
Figure 3:
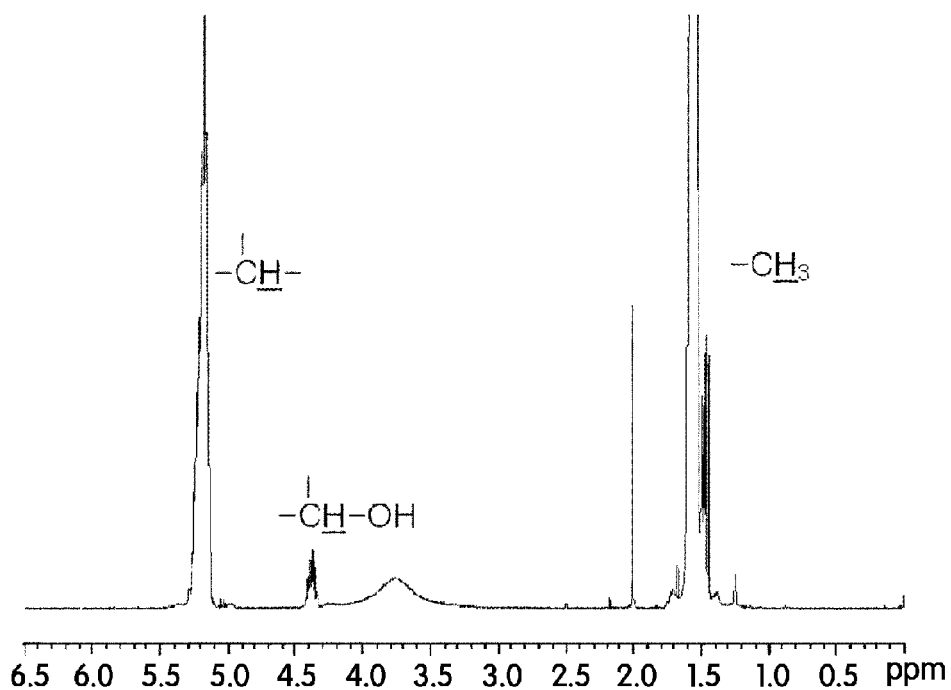

First, 200 mL of acetonitrile was added to 100 g of polylactic acid obtained from Preparation Example 1 to dissolve the polymer. Next, 200 mL of distilled water was added to the polymer solution, and the mixture was agitated at 60° C. under 100 rpm for 2 hours. After the two solvent layers were separated from each other at room temperature, the organic solvent layer was isolated. Then, the organic solvent layer was washed with 100 mL of distilled water to cause additional phase separation, and then the organic solvent layer was collected. The organic solvent layer was subjected to fractional distillation at 80° C. under vacuum to remove the organic solvent. As a result, 73 g of purified polylactic acid was obtained. The purified polylactic acid was analyzed by NMR and the results are shown in FIG. 3.

Example 2

Synthesis and Purification of Sodium Salt of D,L-polylactic Acid (PLA-COONa)

First, 150 mL of acetonitrile was added to 100 g of the polylactic acid obtained from Preparation Example 1 to dissolve the polymer. Next, 150 mL of aqueous sodium bicarbonate solution (0.1 g/mL) was gradually added to the polymer solution, and the mixture was agitated at 60° C. under 100 rpm for 2 hours. Then, 15 g of sodium chloride was added thereto at room temperature and dissolved with agitation. The two solvent layers were separated from each other using a separation funnel and the aqueous layer was discarded.

Then, 100 mL of distilled water and 10 g of sodium chloride were added to the remaining organic solvent layer and dissolved therein with agitation. The two solvent layers were separated again using a separation funnel to collect the organic solvent layer. The organic solvent layer was subjected to fractional distillation at 80° C. under vacuum for 2 hours to completely remove the organic solvent and distilled water.

Figure 4:
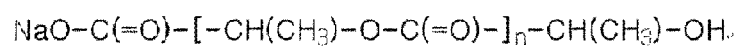
FIG. 4 is the ¹H-NMR spectrum of sodium salt of D,L-polylactic acid purified according to Example 2.
Figure 4:
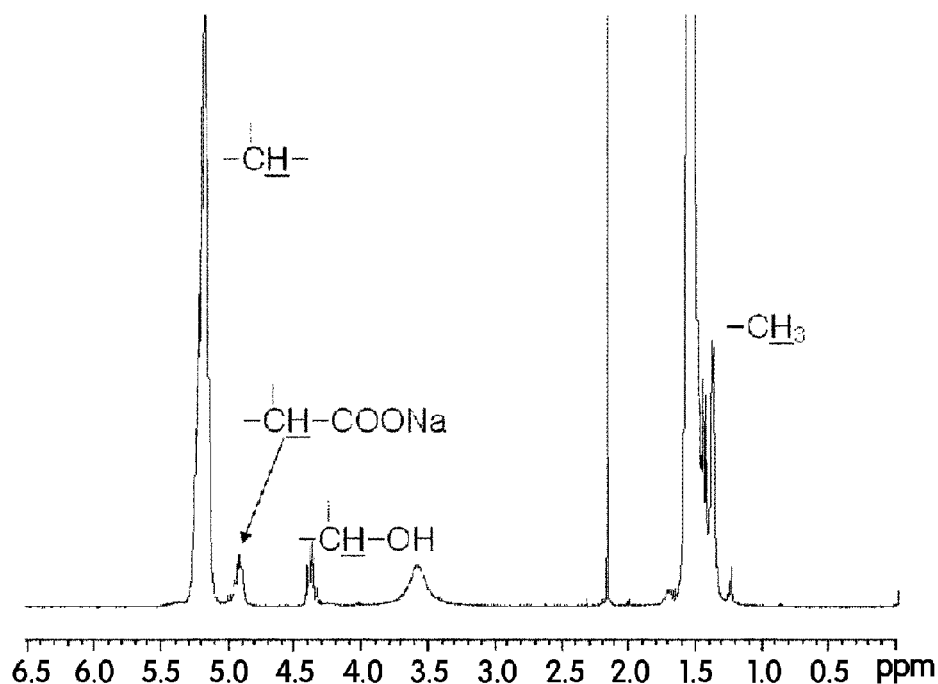

After that, 150 mL of anhydrous acetone was added thereto to dissolve the polymer, and the non-dissolved precipitate was filtered off. The resultant polymer solution was subjected to fractional distillation at 80° C. under vacuum for 2 hours to remove acetone. As a result, 69 g of purified sodium salt of polylactic acid was obtained. The purified sodium salt of polylactic acid was analyzed by NMR and the results are shown in FIG. 4.

Example 3

Synthesis and Purification of Sodium Salt of D,L-polylactic Acid (PLA-COONa)

Example 2 was repeated, except that 100 g of the polylactic acid obtained from Preparation example 2 was used, to obtain 63 g of purified sodium salt of polylactic acid.

Test Example 1

Comparison of Purification Quality

The polylactic acid or derivatives thereof, or salts thereof, prepared or purified according to Preparation Examples 1 and 2, Comparative Examples 1 and 2, and Examples 1, 2 and 3, were analyzed to determine the molecular weight, lactide content and organometal catalyst content in each polymer.

To determine the molecular weight and lactide content of each polymer, $^1$H-NMR analysis was carried out to obtain intensity of hydroxyl groups as terminal groups of polylactic acid. Then, the molecular weight and lactide content were calculated from the intensity. Sn content was analyzed by induction coupled plasma (ICP) emission spectroscopy.

The test results are shown in Table 1.

TABLE 1

|  | Molecular weight (Mn) | Lactide content (wt %) | Sn content (ppm) |
| --- | --- | --- | --- |
| Preparation Example 1 | 1,080 | 4.6 | — |
| Comparative Example 1 | 1,200 | 1.8 | — |
| Example 1 | 1,260 | 0.5 | — |
| Example 2 | 1,285 | Not detected | — |
| Comparative Example 2 | 1,245 | 5.2 | 152 |
| Example 3 | 1,312 | 0.1 | 8.5 |

As can be seen from Table 1, when purifying D,L-polylactic acid having a relatively low molecular weight, lactide is not completely removed by the known method based on a solvent/non-solvent process (Comparative Example 1). Also, in this case, the purified D,L-polylactic acid shows a relatively small increase in molecular weight as compared to the original sample (Preparation Example 1). In addition, when purifying D,L-polylactic acid according to Comparative Example 2, the purified polymer still has a high lactide content and includes a large amount of organometal catalyst remaining after the purification.

On the contrary, according to Examples 1, 2 and 3, the purified polylactic acid has significantly low lactide content and shows a relatively large increase in molecular weight. In addition, Example 3 demonstrates that the organometal catalyst is effectively removed from the purified polylactic acid. Therefore, the above results demonstrate that the method disclosed herein provides a highly purified polylactic acid, or a derivative thereof, or a salt thereof.

INDUSTRIAL APPLICABILITY

The polylactic acid or a derivative thereof, or a salt thereof disclosed herein may be applied to various medical and drug carrier systems, or the like.

While the exemplary embodiments have been shown and described, it will be understood by those skilled in the art that various changes in form and details may be made thereto without departing from the spirit and scope of this disclosure as defined by the appended claims.

In addition, many modifications can be made to adapt a particular situation or material to the teachings of this disclosure without departing from the essential scope thereof. Therefore, it is intended that this disclosure not be limited to the particular exemplary embodiments disclosed as the best mode contemplated for carrying out this disclosure, but that this disclosure will include all embodiments falling within the scope of the appended claims.

The invention claimed is:

1. A method for purifying an alkali metal salt of a polylactic acid homopolymer, consisting of the following steps performed sequentially:
   dissolving a polylactic acid homopolymer which has a number average molecular weight of 500-20,000 daltons into a water-miscible organic solvent which is acetone or acetonitrile;
   adding an aqueous alkali metal salt solution selected from aqueous sodium bicarbonate and aqueous sodium carbonate to the solution of the polymer dissolved in the organic solvent, followed by mixing to produce an alkali metal salt of the polylactic acid, wherein the mixing is carried out by agitating the mixture at 40-100° C. for 10 minutes to 24 hours;
   subjecting the mixture to phase separation by adding sodium chloride or potassium chloride to the mixture so that the mixture is separated into an organic solvent layer and an aqueous layer and to recover the organic solvent layer; and
   removing the organic solvent from the organic solvent layer and recovering the purified alkali metal salt of the polylactic acid,
   and wherein the aqueous alkali metal solution salt has a concentration of 0.05-0.1 g/mL.

2. A method for purifying an alkali metal salt of a polylactic acid homopolymer, consisting of the steps of:
   dissolving a polylactic acid homopolymer which has a number average molecular weight of 500-20,000 daltons into a water-miscible organic solvent selected from acetone or acetonitrile;
   adding an aqueous alkali metal salt solution selected from aqueous sodium bicarbonate and aqueous sodium carbonate to the solution of the polymer dissolved in the organic solvent, followed by mixing to produce an alkali metal salt of the polylactic acid;
   subjecting the mixture to phase separation by adding sodium chloride or potassium chloride to the mixture so that the mixture is separated into an organic solvent layer and an aqueous layer and to recover the organic solvent layer;
   removing the organic solvent from the organic solvent layer and recovering the purified alkali metal salt of the polylactic acid;
   dissolving the recovered polymer into an anhydrous organic solvent, followed by filtering, to obtain a polymer-containing organic solvent; and
   removing the anhydrous organic solvent from the polymer-containing organic solvent,
   wherein the aqueous alkali metal salt solution has a concentration of 0.05-0.1 g/mL,
   wherein the mixing is carried out by agitating the mixture at 40-100° C. for 10 minutes to 24 hours; and
   wherein the steps are performed sequentially.

3. The method for purifying an alkali metal salt of a polylactic acid according to claim 2, wherein the anhydrous organic solvent is anhydrous acetone or anhydrous acetonitrile.

* * * * *